United States Patent [19]

Cordi et al.

[11] Patent Number: 5,424,464

[45] Date of Patent: Jun. 13, 1995

[54] P-[BIS(2-CHLOROETHYL)AMINO]-PHENYLALANINE COMPOUNDS

[75] Inventors: Alex Cordi, Suresnes; Angela D. Morris, Viroflay; Ghanem Atassi, Saint Cloud, all of France

[73] Assignee: Adir et Compagnie, Courbevoie, France

[21] Appl. No.: 170,055

[22] Filed: Dec. 20, 1993

[30] Foreign Application Priority Data

Dec. 21, 1992 [FR] France ............................. 92 15319

[51] Int. Cl.⁶ ............................................ C07C 235/00
[52] U.S. Cl. ...................................... 554/58; 554/227
[58] Field of Search .................... 554/103, 58, 227; 514/908, 724, 613, 616, 630, 552

[56] References Cited

PUBLICATIONS

Deverre et al, Arzneimittel-Forschung. Drug Research. vol. 42, #9, pp. 1153–1156, 1992.
Deverre et al, Proceedings Program Int Symp Controlled Release Bioact Materials, pp. 215–216, 1991.

*Primary Examiner*—Jose G. Dees
*Assistant Examiner*—Deborah D. Carr
*Attorney, Agent, or Firm*—Gordon W. Hueschen

[57] ABSTRACT

Antileukemic compounds of formula (I):

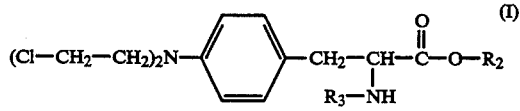

in which:
R¹ represents hydrogen, linear or branched ($C_1$-$C_6$)-alkoxycarbonyl or substituted or unsubstituted phenylalkoxycarbonyl,
R² represents any one of the following groups:

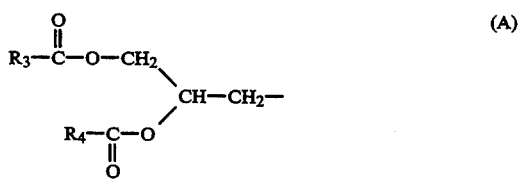

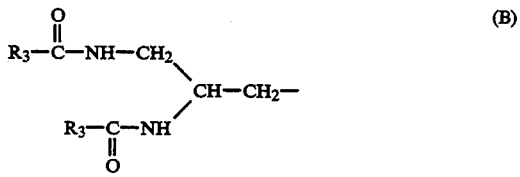

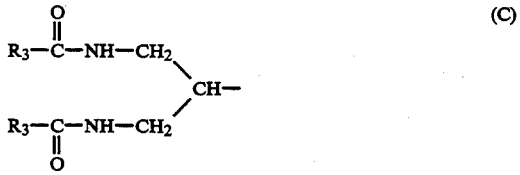

in which:
R₃ or R₄, which are identical or different, represent linear or branched ($C_6$-$C_{19}$)-alkyl or linear or branched ($C_6$-$C_{19}$)-alkenyl, and antileukemic products containing the same.

8 Claims, No Drawings

P-[BIS(2-CHLOROETHYL)AMINO]PHENYLALA- NINE COMPOUNDS

The present invention relates to new p-[bis(2-chloroethyl)amino]phenylalanine compounds.

A certain number of glycerolipid prodrugs have already been described in the literature in fields as diverse as those regarding non-steroidal anti-inflammatory agents, bactericides or even anti-cancer agents. The role of these prodrugs is to reduce, or even suppress, certain side effects of the active ingredients from which they are synthesized.

Glycerolipid prodrugs are intended to target the lymphatic system via the oral route, to avoid hepatic first path effects as well as to enhance the oral bioavailability of certain drugs.

In the field of anti-cancer agents, it was useful to synthesize prodrugs capable of reaching lymphatic-disseminated tumours and/or of crossing the haematoencephalic barrier after oral administration. Such is the case, for example, for the chlorambucil esters described by A. Garzon-Aburdeh (J. Med. Chem., 26, 1200–1203, 1983).

Melphalan prodrugs have, for their part, been described for use in the antiparasitic field (J. R. DEVERRE, Arzneim.Forsch/Drug Res. 42(II), 9, 1153–1156, 1992).

The compounds of the present invention are Melphalan prodrugs which, in addition to the fact that they are new, have a particularly useful pharmacological activity.

More specifically, the present invention relates to the compounds of formula (I):

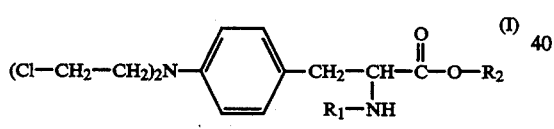

in which:

$R_1$ represents a hydrogen atom, a linear or branched ($C_1$-$C_6$)-alkoxycarbonyl radical or a phenylalkoxycarbonyl radical (unsubstituted or substituted on the phenyl nucleus by one or more halogen atoms or alkyl, alkoxy or trihaloalkyl groups), $R_2$ represents any one of the following groups:

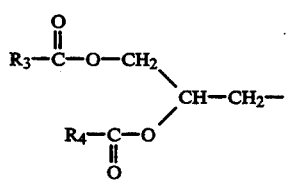

(A)

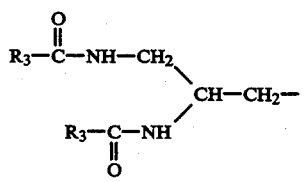

(B)

-continued

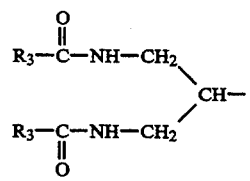

(C)

in which:

$R_3$ or $R_4$, which are identical or different, represent a linear or branched ($C_6$-$C_{19}$)-alkyl radical or a linear or branched ($C_6$-$C_{19}$)-alkenyl radical, to their enantiomers, diastereoisomers and epimers as well as their addition salts with a pharmaceutically acceptable acid.

Among the pharmaceutically acceptable acids, there may be mentioned, with no limitation being implied, hydrochloric, hydrobromic, sulfuric, phosphonic, acetic, trifluoroacetic, lactic, pyruvic, malonic, succinic, glutaric, fumaric, tartaric, maleic, citric, ascorbic, methanesulfonic and camphoric acids and the like.

The invention also extends to the process for preparing the compounds of formula (I).

The process for preparing the compounds of formula (I) in which $R_2$ represents the group (A) is characterized in that there is used as starting material the p-[bis(2-chloroethyl)amino]phenylalanine of formula (II), in racemic form or in the form of a pure enantiomer, whose amine functional group has been protected by a conventional protecting group:

in which $R'_1$ represents a linear or branched ($C_1$-$C_6$)-alkoxycarbonyl radical or a phenylalkoxycarbonyl radical (unsubstituted or substituted on the phenyl nucleus by one or more halogen atoms or alkyl, alkoxy or trihaloalkyl groups), which is reacted with the 1,3-dioxolane of formula (III) in racemic form or in the form of a pure enantiomer:

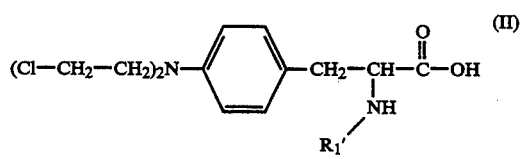

in the presence of a coupling agent for peptide synthesis such as benzotriazol-1-yloxytris(dimethylamino)phosphonium hexafluorophosphate (BOP) (according to the technique described in Tet. Lett. 1219, 1975) and diisopropylethylamine in dichloromethane, to give the 1,3-dioxolane of formula (IV):

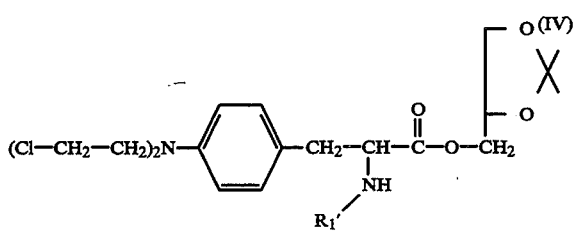

in which $R'_1$ has the same meaning as above, which is converted, in acidic medium, to the corresponding diol of formula (V):

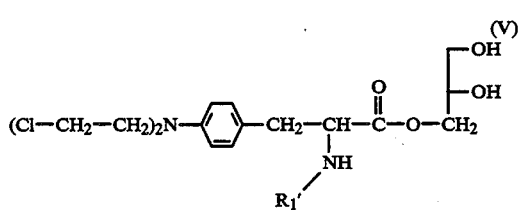

in which $R'_1$ has the same meaning as above, which is reacted, according to the nature of the compounds of formula (I) which it is desired to obtain, with:

either, in the case where $R_3$ and $R_4$ are identical: 2 equivalents of the acid chloride of formula (VI), in the presence of a base, $$R_3\text{—CO—Cl} \qquad (VI)$$

in which $R_1$ has the same meaning as in formula (I), to give the compound of formula (I/a), which is a specific example of the compounds of formula (I),

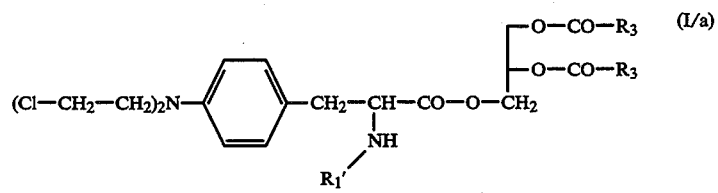

in which $R'_1$ and $R_3$ have the same meaning as above, or, in the case where $R_3$ and $R_4$ are different: with one equivalent of the acid chloride of formula (VI) described above, to give, after separation of the mono- and diacylated compounds, the compound of formula:

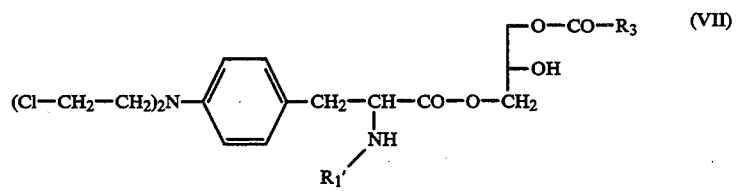

in which $R'_1$ and $R_3$ have the same meaning as above, which is reacted with one equivalent of the acid chloride of formula (VIII) in the presence of a base:

$$R_4\text{—CO—Cl} \qquad (VIII)$$

to give the compound of formula (I/b), which is a specific example of the compounds of formula (I),

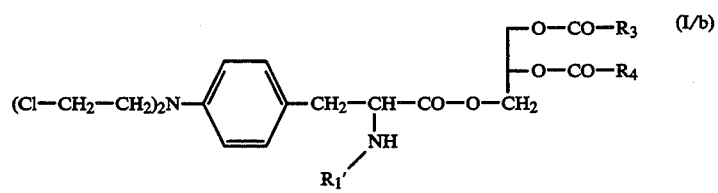

in which $R'_1$, $R_3$ and $R_4$ have the same meaning as above, which compounds of formula (I/a) or (I/b), which can undergo, if desired, an acid hydrolyis or a hydrogenolysis to give the compounds of formula (I/c) or (I/d) respectively, which are specific examples of the compounds of formula (I):

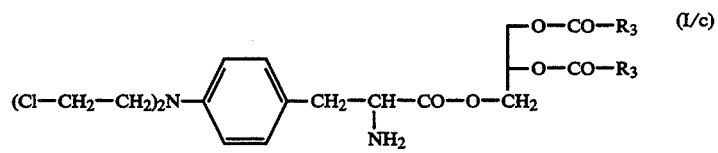

-continued

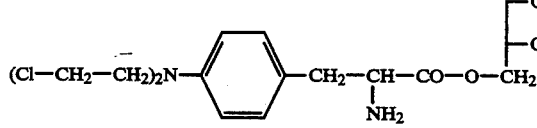 (I/d)

in which $R_3$ and $R_4$ have the same meaning as in formula (I), compounds of formula (I/a), (I/b), (I/c) or (I/d):
- which are purified, where appropriate, according to a conventional purification technique,
- whose isomers are separated, if desired, according to a conventional purification technique,
- and which are optionally converted to their addition salts with a pharmaceutically acceptable acid.

Another process for the synthesis of the compounds of formula (I) in which $R_2$ represents the group (A) is

 (IX)

in which $R_3$ and $R_4$ have the same meaning as in formula (I), which is reacted, in the presence of a coupling agent for peptide synthesis such as benzotriazol-1-yloxytris(-dimethylamino)phosphonium hexafluorophosphate (BOP) (according to the technique described in Tet. Lett. 1219, 1975) and diisopropylethylamine in dichloromethane, with the p-[bis(2-chloroethyl)amino]-phenylalanine of formula (II), in racemic form or in the form of a pure enantiomer, whose amine functional group has been protected by a conventional protecting group:

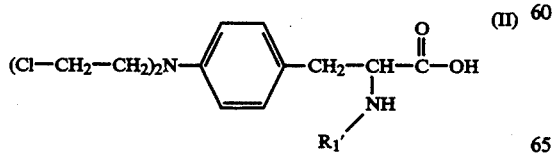 (II)

in which $R'_1$ represents a linear or branched ($C_1$-$C_6$)-alkoxycarbonyl radical or a phenylalkoxycarbonyl radical (unsubstituted or substituted on the phenyl nucleus by one or more halogen atoms or alkyl, alkoxy or trihaloalkyl groups), to give the compound of formula (I'), which is a specific example of the compounds of formula (I):

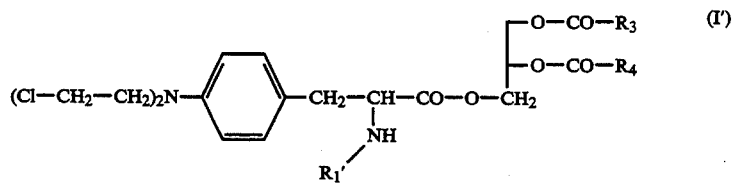 (I')

in which $R'_1$, $R_3$ and $R_4$ have the same meaning as above, which can be subjected, if desired, to an acid hydrolysis or a hydrogenolysis, to give respectively the compound of formula (I''), which is a specific example of the compound of formula (I):

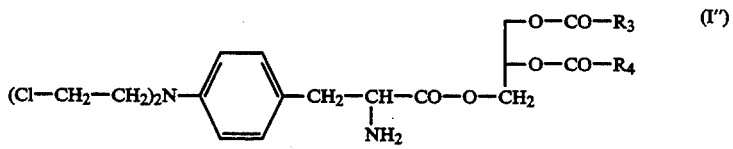 (I'')

in which $R_3$ and $R_4$ have the same meaning as in formula (I),
compounds of formula (I') or (I''):
- which are purified, where appropriate, according to a conventional purification technique,
- whose isomers are separated, if desired, according to a conventional purification technique,
- and which are optionally converted to their addition salts with a pharmaceutically acceptable acid.

The process for preparing the compounds of formula (I) in which $R_2$ represent the group (B) or (C) is characterized in that there is used as starting material the p-[bis(2-chloroethyl)amino]phenylalanine of formula (II), in racemic form or in the form of a pure enantiomer, whose amine functional group has been protected by a conventional protecting group:

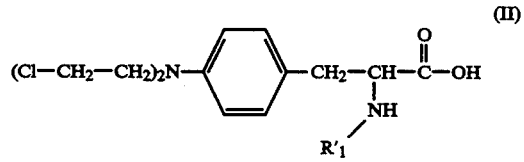 (II)

in which $R'_1$ represents a linear or branched ($C_1$-$C_6$)-alkoxycarbonyl radical or a phenylalkoxycarbonyl radical (unsubstituted or substituted on the phenyl nucleus by one or more halogen atoms or alkyl, alkoxy or trihaloalkyl groups),
which is reacted in the presence of isoprenyl chloroformate, triethylamine and 4-dimethylaminopyridine:
either, with the compound of formula (Xa):

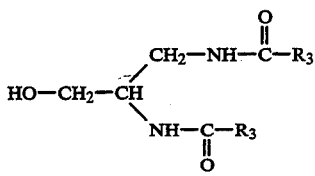

or, with the compound of formula (Xb):

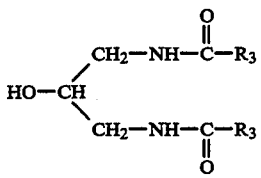

to give the compounds of formula (I/e) or (I/f) respectively, which are specific examples of the compounds of formula (I):

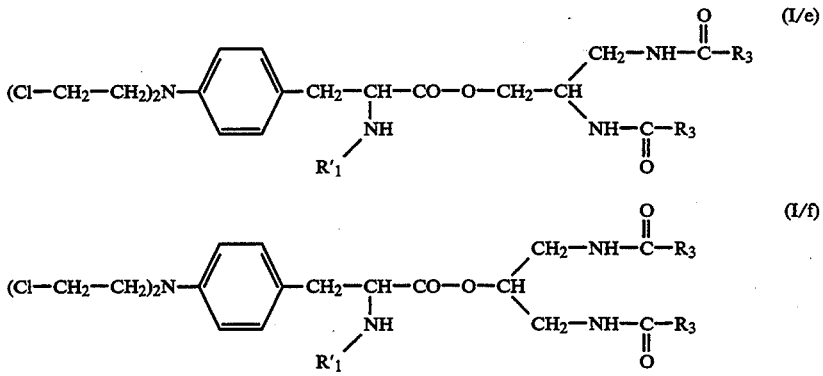

which compounds of formula (I/e) or (I/f) can be subjected, if desired, to an acid hydrolysis or a hydrogenolysis, to give the compounds of formula (I/g) or (I/h) respectively, which are specific examples of the compounds of formula (I):

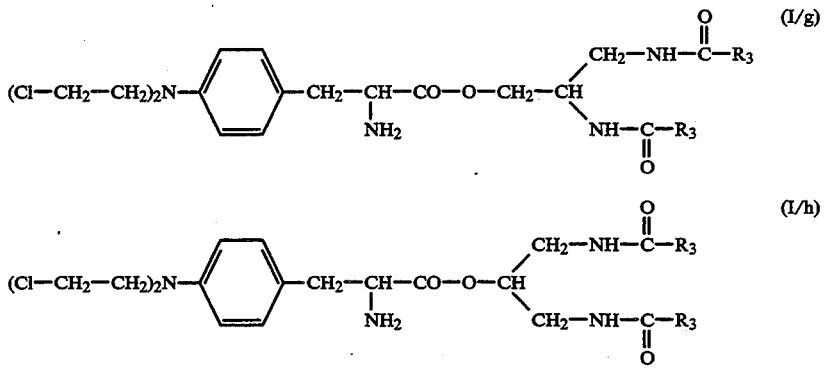

compounds of formula (I/e), (I/f), (I/g) or (I/h):
which are purified, where appropriate, according to a conventional purification technique,
whose isomers are separated, if desired, according to a conventional purification technique,
and which are optionally converted to their addition salts with a pharmaceutically acceptable acid.

These new p-[bis(2-chloroethyl)amino]phenylalanine compounds possess very useful pharmacological properties. They possess, on the one hand, an activity which is substantially greater than that of the active ingredient from which they are synthesized, and, on the other hand, a substantially lower toxicity.

The invention also extends to the pharmaceutical compositions containing, as active ingredient, at least one compound of formula (I) or its optical isomers with one or more inert, nontoxic and appropriate excipients. The pharmaceutical compositions thus obtained can be provided in various forms, the most advantageous being tablets, sugar-coated tablets, hard gelatine capsules, suppositories, suspensions to be taken orally and the like.

The useful dosage can be adapted according to the nature and severity of the condition, the route of administration as well as the age and weight of the patient. This unit dosage ranges from 10 mg to 1 g per day in single or divided doses.

The following examples illustrate the invention and do not limit it in any manner.

The starting materials used are known materials or materials prepared according to known procedures.

EXAMPLE 1:
1,2-Distearoyl-3-{(S)-N-tert-butoxycarbonyl-4-[bis(2-chloroethyl)amino]phenylalanyl}glycerol Stage A:

(S)-N-tert-Butoxycarbonyl-4-[bis(2-chloroethyl)amino]phenylalanine 11 mmol of di-tert-butyl dicarbonate are added to a solution, maintained at 0° C., with stirring, containing 10 mmol of (S)-4-[bis(2-chloroethyl)amino]phenylalanyl in 20 ml of dioxane, 10 ml of water and 11 ml of 1N NaOH. After stirring for 16 hours at 20° C., the whole mixture is concentrated and the residue is taken up in 12 ml of water and 75 ml of ethyl acetate. The pH is adjusted to 2 and the aqueous phase extracted with 3×200 ml of ethyl acetate. The organic phase is washed with 200 ml of water and 200 ml of a saturated sodium chloride solution, dried and then concentrated under vacuum.

Stage B:
1,2-Distearoyl-3-{(S)-N-tert-butoxycarbonyl-4-[bis(2-chloroethyl)amino]phenylalanyl}glycerol 8 mmol of the compound obtained in the preceding stage, 8 mmol of benzotriazol-1-yloxytris(dimethylamino)phosphonium hexafluorophosphate and 8 mmol of 1,2-distearoylglycerol are mixed in 50 ml of dichloromethane. 16 mmol of diisopropylethylamine are added and the solution is stirred at 20° C. for 16 hours. The mixture is diluted with 150 ml of dichloromethane and then washed with 3×80 ml of a saturated sodium chloride solution. The organic phase is dried and then concentrated under vacuum. The product is obtained, in solid form, after purification of the residue by silica gel chromatography using dichloromethane as eluent.
Melting point: 51°–52° C.
Elemental microanalysis:

|  | C % | H % | N % | Cl % |
|---|---|---|---|---|
| Calculated | 67.63 | 9.96 | 2.77 | 7.00 |
| Found | 67.59 | 9.67 | 3.07 | 7.30 |

EXAMPLE 2:
1,2-Distearoyl-3-{(S)-4-[bis(2-chloroethyl)amino]phenylalanyl}glycerol A solution of 5 mmol of the product obtained in Example 1 in 25 ml of hydrogen chloride-saturated dioxane is stirred for 20 minutes at 20° C. The whole mixture is concentrated under vacuum and the residue is washed with pentane, to give the expected product in hydrochloride form.
Melting point: 82°–83° C.
Elemental microanalysis:

|  | C % | H % | N % | Cl % |
|---|---|---|---|---|
| Calculated | 65.84 | 9.88 | 2.95 | 11.21 |
| Found | 65.50 | 9.70 | 3.08 | 11.27 |

The compounds of Examples 3 and 4 were obtained according to the same procedure as that of Example 1, using the corresponding starting materials.

EXAMPLE 3:
1,2-Dipalmitoyl-3-{(S)-N-tert-butoxycarbonyl-4-[bis(2-chloroethyl)amino]phenylananyl}glycerol
Melting point: 36°–37° C.
Elemental microanalysis:

|  | C % | H % | N % | Cl % |
|---|---|---|---|---|
| Calculated | 66.57 | 9.70 | 2.93 | 7.42 |
| Found | 66.44 | 9.32 | 3.27 | 7.58 |

EXAMPLE 4:
1,2-Dimyristoyl-3-{(S)-N-tert-butoxycarbonyl-4-[bis(2-chloroethyl)amino]phenylalanyl}glycerol
Melting point: oil
Elemental microanalysis:

|  | C % | H % | N % | Cl % |
|---|---|---|---|---|
| Calculated | 65.38 | 9.41 | 3.11 | 7.88 |
| Found | 65.38 | 9.32 | 3.47 | 8.21 |

EXAMPLE 5:
1,2-Dipalmitoyl-3-{(S)-4-[bis(2-chloroethyl)amino]phenylalanyl}glycerol This compound was obtained according to the procedure described in Example 2, from the compound of Example 3.
Melting point: 85°–86° C.
Elemental microanalysis:

|  | C % | H % | N % | Cl % |
|---|---|---|---|---|
| Calculated | 64.59 | 9.60 | 3.14 | 11.92 |
| Found | 64.21 | 9.66 | 3.15 | 11.67 |

EXAMPLE 6:
1,2-Dimyristoyl-3-{(S)-4-[bis(2-chloroethyl)amino]phenylalanyl}glycerol This compound was obtained according to the procedure described in Example 2, from the compound of Example 4.
Melting point: 91°–92° C.
Elemental microanalysis:

|  | C % | H % | N % | Cl % |
|---|---|---|---|---|
| Calculated | 63.18 | 9.28 | 3.35 | 12.72 |
| Found | 62.65 | 9.00 | 3.31 | 12.59 |

EXAMPLE 7:
2,3-Bis(palmitoylamino)-(O)-{(S)-N-tert-butoxycarbonyl-4-[bis(2-chloroethyl)amino]phenylalanyl}propan-1-ol 8 mmol of (S)-N-tert-butoxycarbonyl-4-[bis(2-chloroethyl)amino]phenylalanine, 8.8 mmol of 2,3-bis(palmitoylamino)propan-1-ol, 8.8 mmol of triethylamine, 4.4 mmol of 4-dimethylaminopyridine are mixed in 500 ml of tetrahydrofuran at 35°–40° C. for 20 minutes. 8.8 mmol of isoprenyl chloroformate are added and the solution is stirred for 90 minutes. The whole mixture is then concentrated and the residue is taken up in 100 ml of dichloromethane, washed with 100 ml of water and then with a 10% sodium bicarbonate solution and finally with a saturated sodium chloride solution. The organic phase is dried and then concentrated under vacuum. The expected product is then obtained, in solid form, after purification of the residue by silica gel chromatography, using a dichloromethane/ethanol mixture (95/5) as eluent.
Melting point: 79°–80° C.

EXAMPLE 8:

2,3-Bis(palmitoylamino)-(O)-{(S)-4-[bis(2-chloroethyl)amino]phenylalanyl}propan-1-ol, hydrochloride A solution containing 5 mmol of the product described in Example 7 in 25 ml of dioxane saturated with gaseous hydrochloric acid is stirred for 20 minutes at 20° C. After concentration of the solvent, the expected product is obtained in hydrochloride form.

Melting point: 130°–132° C.

Elemental microanalysis:

|  | C % | H % | N % |
|---|---|---|---|
| Calculated | 64,73 | 9,85 | 6,29 |
| Found | 64,42 | 9,56 | 6,00 |

EXAMPLE 9:

1,3-Bis(palmitoylamino)-(O)-{(S)-N-tert-butoxycarbonyl-4-[bis(2-chloroethyl)amino]phenylalanyl}isopropanol The expected product is obtained according to the procedure described in Example 7, replacing 2,3-bis(palmitoylamino) propan-1-ol with 1,3-bis(palmitoylamino)isopropanol.

Melting point: 88°–89° C.

EXAMPLE 10:

1,3-Bis(palmitoylamino)-(O)-{(S)-4-[bis(2-chloroethyl)amino]phenylalanyl}isopropanol The expected product is obtained according to the procedure described in Example 8, using the compound of Example 9.

Melting point: 153°–155° C.

Elemental microanalysis:

|  | C % | H % | N % | Cl % |
|---|---|---|---|---|
| Calculated | 64.73 | 9.85 | 6.29 | 11.24 |
| Found | 64.57 | 9.82 | 6.10 | 12.11 |

PHARMACOLOGICAL STUDY OF THE COMPOUNDS OF THE INVENTION

EXAMPLE 11: Evaluation of the antitumour activity on P388 leukaemia (i.p.)

The study was carried out according to the following procedure:

$10^6$ leukaemic cells (P388) are intraperitoneally (i.p.) inoculated on day 0 into female BDFa mice with an average weight of between 18 and 22 g.

The products are administered, on day 1, by the i.p. route, in a single dose.

The criteria for activity are the number of long term survivors in the treated groups and the T/C ratio %:

$$\frac{T}{C}(\%) = \frac{\text{median survival of the treated mice}}{\text{median survival of the control mice}}$$

The T/C ratio should be greater than or equal to 125% and a T/C ratio of less than or equal to 95% indicates the presence of general toxicity as was shown by GERAN R.I. et al. (Cancer Chemoter. Rep. 3 (3), 1–100, 1972).

The results collated below show that these prodrugs possess a particularly potent activity combined with a substantially lower toxicity than that of melphalan.

| Example | Dose (mg/kg) | Var. Weight (g) D1–D5 | Med. T/C (%) | Survival at D35 |
|---|---|---|---|---|
| 2 | 46.6 | +0.5 | 199 | 0/5 |
|  | 93.3 | −1.0 | 273 | 1/5 |
| 5 | 43.9 | +0.2 | 245 | 2/5 |
|  | 87.8 | −0.5 | >330 | 5/5 |
| 6 | 20.4 | +0.7 | >330 | 6/8 |
|  | 40.8 | +0.4 | >330 | 8/8 |
|  | 81.7 | −2.7 | >330 | 8/8 |
| Melphalan | 7.5 | +0.6 | 231 | 3/8 |
|  | 15 | +0.1 | >330 | 7/8 |
|  | 30 | −4.2 | 93 | 2/8 |
| Controls | — | +2.6 | 100 | 0/24 |

(The doses indicated in this table are calculated in Melphalan EQUIVALENTS).

EXAMPLE 12: Pharmaceutical composition

Preparation formula for 1000 tablets in 100 mg doses:

| Compound of Example 2 | 100 g |
|---|---|
| Hydroxypropyl cellulose | 2 g |
| Wheat starch | 10 g |
| Lactose | 100 g |
| Magnesium stearate | 3 g |
| Talc | 3 g |

We claim:

1. A compound of formula (I):

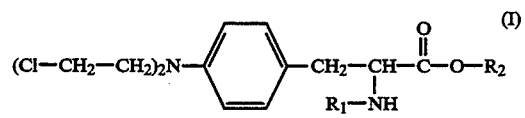

in which:

$R_1$ represents hydrogen, linear or branched ($C_1$–$C_6$)-alkoxycarbonyl or phenylalkoxycarbonyl (unsubstituted or substituted on the phenyl nucleus by one or more halogen, alkyl, alkoxy or trihaloalkyl), $R_2$ represents any one of the following groups:

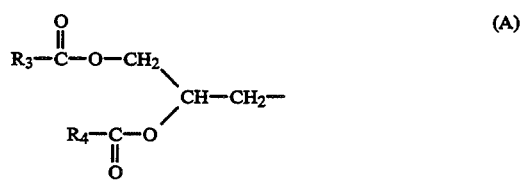

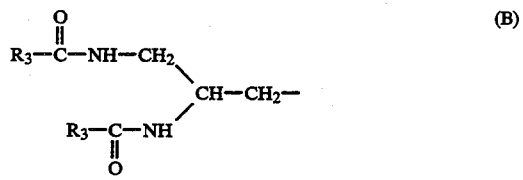

-continued

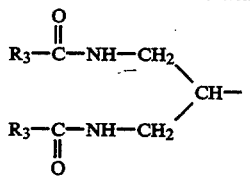

in which:
R$_3$, and R$_4$, which are identical or different, represent linear or branched (C$_6$–C$_{19}$)-alkyl or linear or branched (C$_6$–C$_{19}$)-alkenyl, their enantiomers, diastereoisomers, or epimers or their addition salts with a pharmaceutically acceptable acid.

2. A compound of claim 1, in which R$_2$ represents the group

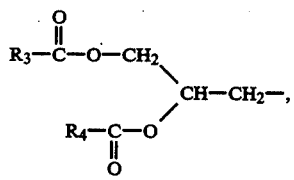

its enantiomers, diastereoisomers, or its addition salts with a pharmaceutically-acceptable acid.

3. A compound of claim 1, in which R$_3$-CO and R$_4$-CO, which are identical, each represent stearoyl, its enantiomers, diastereoisomers, or its addition salts with a pharmaceutically-acceptable acid.

4. A compound of claim 1, in which R$_3$-CO and R$_4$-CO, which are identical, each represent myristoyl, its enantiomers, diastereoisomers, or its addition salts with a pharmaceutically-acceptable acid.

5. A compound of claim 1, in which R$_3$-CO and R$_4$-CO, which are identical, each represent palmitoyl, its enantiomers, diastereoisomers, or its addition salts with a pharmaceutically-acceptable acid.

6. A compound of claim 1, in which R$_1$ represents hydrogen, its enantiomers, diastereoisomers, or its addition salts with a pharmaceutically-acceptable acid.

7. A method for treating a mammal afflicted with leukemia comprising the step of administering to the mammal an amount of a compound of claim 1 which is effective for ameloration of said leukemia.

8. A pharmaceutical composition useful in treating leukemia comprising as active principle an effective amount of a compound as claimed in claim 1, together with one or more pharmaceutically-acceptable excipients or vehicles.

* * * * *

UNITED STATES PATENT AND TRADEMARK OFFICE
CERTIFICATE OF CORRECTION

PATENT NO. : 5,424,464
DATED : June 13, 1995          Page 1 of 2
INVENTOR(S) : Alex Cordi, Angela D. Morris, Ghanem Atassi It is certified that error appears in the above-indentified patent and that said Letters Patent is hereby corrected as shown below:

TITLE PAGE [57] ABSTRACT; (Formula (I)) "$R_3$" should read -- $R_1$ --.
Col. 2, line 51; Add -- ) -- to end of line.
  line 22
Col. 2, line 52; Delete ")" at beginning of line.
Col. 3, line 12          (last line of formula); $R_1'$ should read -- $R'_1$ -- (Pg 4, line 4)
Col. 3, line 44          (last line of formula); "$R_1'$" should read -- $R'_1$ --
Col. 4, line 5; "$R_3$" should read -- $R_1$ --.
Col. 4, last line of formula (I/a); "$R_1'$" should read -- $R'_1$ --    last line in formula.
Col. 4, Last line of formula (VII); "$R_1'$" should read -- $R'_1$ --
Col. 4, Last line of formula (I/b); "$R_1'$" should read -- $R'_1$ --
Col. 5, line 50; Delete "(" from end of line but keep the dash.
Col. 5, line 51; Add -- ( -- to the beginning of the line.
Col. 5, line 65; "$R_1'$" should read -- $R'_1$ --.

Col. 6, Last line of formula (I'); "$R_1'$" should read -- $R'_1$ --.    last line of formula (I')
Col. 8, line 43; Delete "Stage A:"
Col. 8, line 61; Add -- Stage A: -- to beginning of the line.
Col. 8, line 62; Add -- ) -- to end of line before the dash.

UNITED STATES PATENT AND TRADEMARK OFFICE
CERTIFICATE OF CORRECTION

PATENT NO. : 5,424,464
DATED : June 13, 1995
INVENTOR(S) : Alex Cordi, Angela D. Morris, Ghanem Atassi It is certified that error appears in the above-indentified patent and that said Letters Patent is hereby corrected as shown below:

Col. 8, line 63; Delete ")" at beginning of line.

Col. 11, line 2 from top; Add -- ) -- to end of line before the dash.
Col. 11, line 3 (from top of page); Delete ")" from beginning of line. Pg. 14, line 24
Col. 11, line 25; Delete "(" at end of line but keep dash.
Col. 11, line 26; Add -- ( -- to beginning of line. Pg. 15, line 5
Col. 11, line 31; Add -- ) -- to end of line before the dash.
Col. 11, line 32. Delete ")" from beginning of line.

Col. 13, line 16 (approx); Add -- - --(dash) after pharmaceutically.

Signed and Sealed this

Twenty-sixth Day of September, 1995

Attest:

BRUCE LEHMAN

*Attesting Officer*    *Commissioner of Patents and Trademarks*